United States Patent
Ken et al.

(10) Patent No.: US 9,084,866 B2
(45) Date of Patent: Jul. 21, 2015

(54) BOTTLE AND DIP TUBE

(75) Inventors: Yuki Ken, Osaka (JP); Haramiishi Yoshihisa, Osaka (JP); Shimotoso Toshihiko, Osaka (JP)

(73) Assignee: Japan Medicalnext Co., Ltd., Osaka (JP)

( * ) Notice: Subject to any disclaimer, the term of this patent is extended or adjusted under 35 U.S.C. 154(b) by 231 days.

(21) Appl. No.: 13/876,432

(22) PCT Filed: Sep. 15, 2011

(86) PCT No.: PCT/JP2011/071150
§ 371 (c)(1),
(2), (4) Date: Mar. 27, 2013

(87) PCT Pub. No.: WO2012/043265
PCT Pub. Date: Apr. 5, 2012

(65) Prior Publication Data
US 2013/0200537 A1    Aug. 8, 2013

(30) Foreign Application Priority Data
Sep. 29, 2010    (JP) .................................. 2010-219280

(51) Int. Cl.
*B01F 3/04*    (2006.01)
*A61M 16/16*    (2006.01)
*A61M 11/06*    (2006.01)

(52) U.S. Cl.
CPC .............. *A61M 16/16* (2013.01); *B01F 3/0412* (2013.01); *B01F 3/04106* (2013.01); *B01F 3/04241* (2013.01); *A61M 11/06* (2013.01)

(58) Field of Classification Search
CPC .... B01F 3/04; B01F 3/04099; B01F 3/04106; B01F 3/0412; B01F 3/04241; B01F 3/04248; B01F 2003/0429; A61M 15/00
USPC .............. 261/77, 119.1, 121.1, 126, DIG. 65; 128/200.11, 200.21
See application file for complete search history.

(56) References Cited

U.S. PATENT DOCUMENTS

| | | | |
|---|---|---|---|
| 2,342,602 A | * | 2/1944 | Reitz, Jr. .................. 128/200.13 |
| 2,847,248 A | | 8/1958 | Schmitt et al. |
| 4,045,525 A | * | 8/1977 | Huggins ....................... 261/124 |

FOREIGN PATENT DOCUMENTS

| JP | 2004-057296 A | 2/2004 |
|---|---|---|
| JP | 2004-141493 A | 5/2004 |
| JP | 2004-188120 A | 7/2004 |

OTHER PUBLICATIONS

International Search Report issued in PCT/JP2011/071150 mailed on Jan. 17, 2012 (2 pages).

* cited by examiner

*Primary Examiner* — Robert A Hopkins
(74) *Attorney, Agent, or Firm* — Osha Liang LLP

(57) ABSTRACT

A bottle includes a bottle main body having a bottle mouth portion at an upper part, and a dip tube dipped into a liquid stored in the bottle main body. An upper end of the dip tube is arranged on an inner side of a peripheral wall of the bottle mouth portion with a void part that communicates inside and outside of the bottle main body provided through the bottle mouth portion.

8 Claims, 12 Drawing Sheets

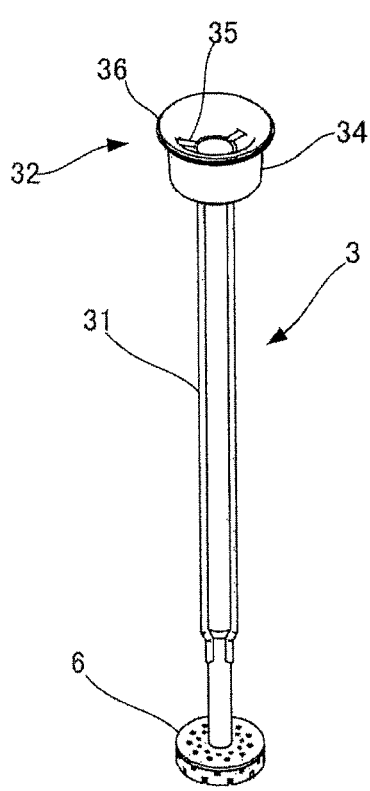
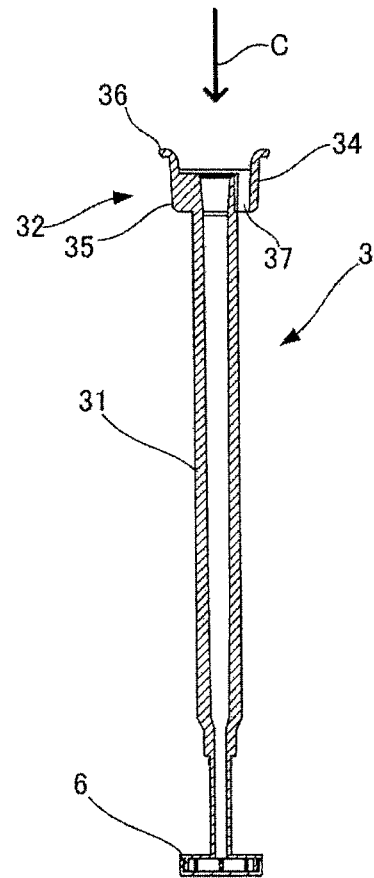
FIG. 7(a)  FIG. 7(b)
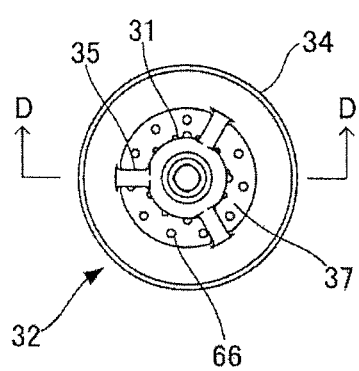
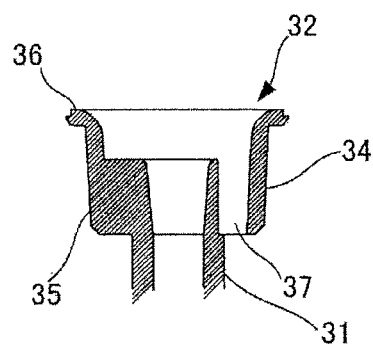
FIG. 7(c)  FIG. 7(d)

BOTTLE AND DIP TUBE

TECHNICAL FIELD

The present invention relates to a bottle, in particular, to a bottle used in a humidifying device that adds moisture (water vapor or mist water) to gas such as air, oxygen, and a dip tube used in the bottle.

BACKGROUND ART

Conventionally, oxygen therapy of supplying oxygen is performed on a patient having problems in the respiratory system, and for example, oxygen generated by an oxygen tank or the like, or oxygen concentrated by an oxygen concentrating device including an adsorbent material such as molecular sieve or the like is supplied to the patient using a nasal cannula, mask or the like. The oxygen supplied from the oxygen tank barely contains moisture, and thus the inside of the respiratory tract needs to be prevented from becoming dry when supplying oxygen into the respiratory tract such as the nasal cavity of the patient. A humidifying device is thus arranged in the middle of the oxygen supplying tube to supply humidified oxygen.

In the oxygen treatment, a nebulizer (aerosol) and a humidifier (humidifying unit) are known for the humidifying device used to humidify the oxygen. These humidifying devices have a configuration of including a bottle (container) for accommodating solution dissolved with medicinal agent, and liquid such as sterilized water, purified water, distilled water, normal saline solution, and the like; and a dedicated humidifying device adapter (nebulizer adapter or humidifier adapter) to be connected to the bottle. The nebulizer or the humidifier are used according to the treatment policy on the patient. The nebulizer is a humidifying device configured to supply oxygen gas into the humidifying device adapter to take in air when aspirating the sterilized water accommodated in the bottle, humidify the gas having high oxygen concentration with the aspirated sterilized water as microscopic aerosol, and supply the humidified gas to the patient. The humidifier, on the other hand, is a humidifying device configured to discharge air or oxygen gas having high oxygen concentration into the sterilized water in the bottle to humidify the gas, and supply the humidified gas to the patient by guiding the humidified gas to outside the bottle.

The nebulizer and the humidifier are different in the mechanism of humidifying the gas but are common in using the bottle accommodating the sterilized water, and thus the bottle is preferably used in common. Patent document 1 discloses a commonly used bottle, that is, a bottle (container) capable of being used for the nebulizer or for the humidifier.

Figure 12:
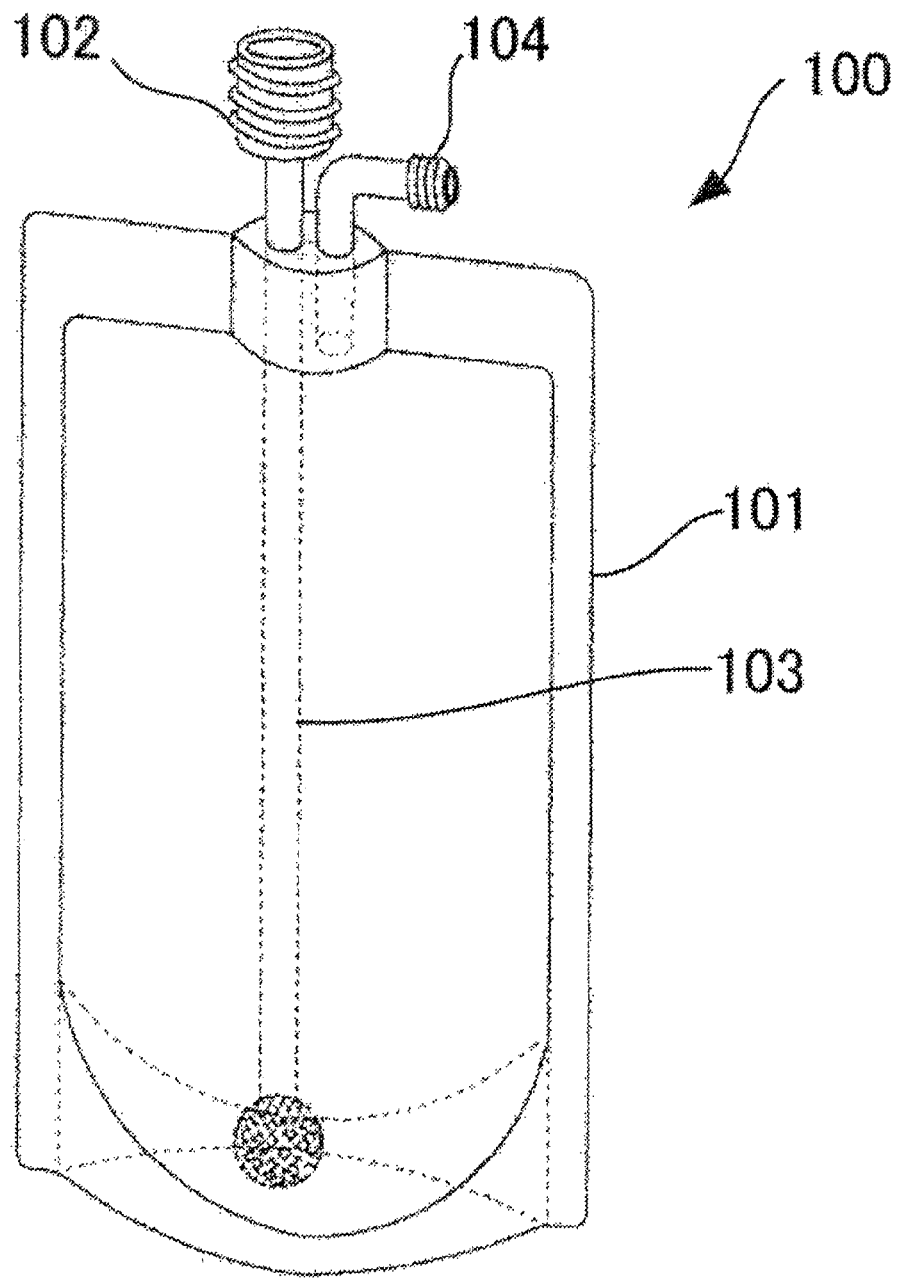

As shown in FIG. 12, the container disclosed in patent document 1 includes a bag main body 101 that accommodates the sterilized water; a first mouth portion 102 that is sealably attached to an upper part of the bag main body 101 and that introduces the oxygen into the bag main body 101, a dip tube 103 that guides the oxygen introduced from the first mouth portion 102 into water, and a second mouth portion 104 that is sealably attached to the upper part of the bag main body 101 and that feeds the oxygen added with moisture obtained on the water surface to outside.

Figures 13A, 13B:
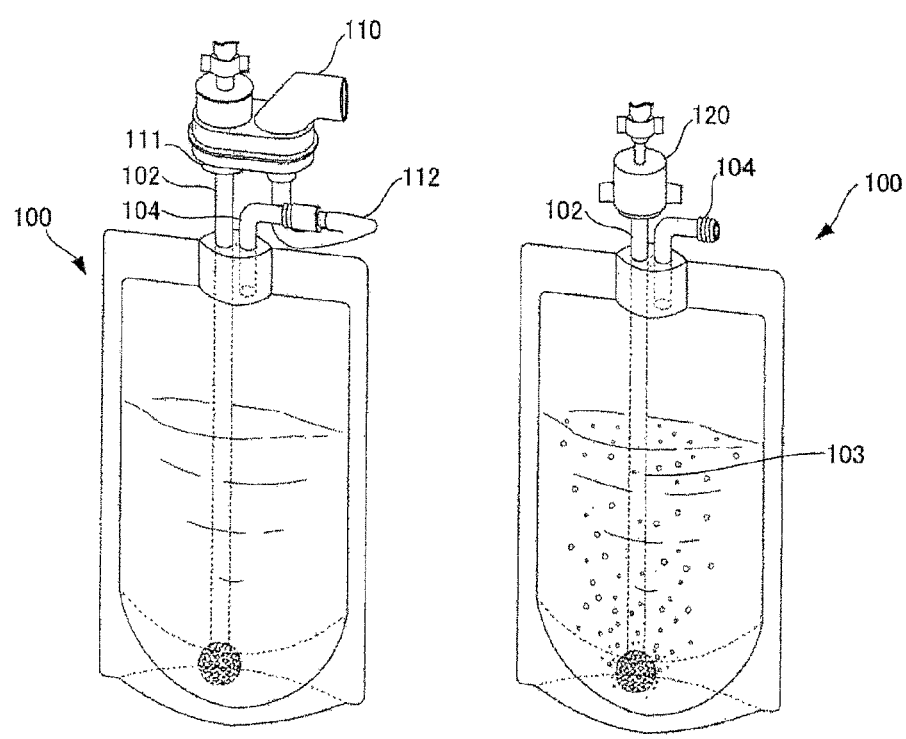

When using the container 100 as a container for the nebulizer, a socket portion 111 of a nebulizer adapter 110 is screw-fitted and connected to the first mouth portion 102 of the container 100, and a drain tube 112 of the nebulizer adapter 110 is connected to the second mouth portion 104 of the container, as shown in FIG. 13(a).

When using the container as a container for the humidifier, on the other hand, a humidifier adapter 120 is fitted to the first mouth portion 102 to communicate with an oxygen supply source (not shown), and a tube (not shown) is connected to the second mouth portion 104 to supply the oxygen added with moisture to the patient, as shown in FIG. 13(b). The oxygen gas supplied from the oxygen supply source is discharged into the water in the container through the dip tube 103 to be humidified, and then supplied to the patient through the second mouth portion 104 and the tube (not shown).

PRIOR ART DOCUMENT

Patent Document

Patent Document 1: Japanese Unexamined Patent Publication No. 2004-141493

SUMMARY OF THE INVENTION

Problems to be Solved by the Invention

The container described above is assumed to have high usability since it can be used as the container for the nebulizer or as the container for the humidifier. However, such container is based on the assumption of connecting the drain tube of the nebulizer adapter as a structure for returning the water droplets accumulated in the nebulizer adapter to the container when being used for the nebulizer. Thus, in a state that the adapter is connected to the container, human hands, objects, and the like may get caught at the drain tube that exists outside the container, which may cause the nebulizer to fall. Since the drain tube is connected to the nebulizer adapter to be connected to the container, the drain tube becomes a hindrance when screw-fitting and connecting the socket portion of the nebulizer adapter to the first mouth portion of the container, and hence the handling of the connection task is very bad. Furthermore, after connecting the nebulizer adapter to the first mouth portion of the container, the drain tube needs to be connected to the second mouth portion of the container, and thus the setting of the nebulizer adapter is troublesome. The container also has a problem in that the manufacturing process of the container is complicating since the second mouth portion, to which the drain tube or the tube to be guided toward the patient is connected, is arranged in addition to the first mouth portion, to which each adapter is connected.

It is an object of the present invention to provide a bottle that can be used for the nebulizer or for the humidifier, and that can return the water droplets accumulated in the nebulizer adapter without using the drain tube when used for the nebulizer, and a dip tube used in the bottle.

Means for Solving the Problems

The object of the present invention is achieved with a bottle including a bottle main body having a bottle mouth portion at an upper part, and a dip tube dipped into a liquid stored in the bottle main body, wherein an upper end of the dip tube is arranged on an inner side of a peripheral wall of the bottle mouth portion with a void part that communicates inside and outside of the bottle main body provided through the bottle mouth portion.

The bottle described above has a structure in which the upper end of the dip tube arranged inside the bottle is arranged on the inner side of the peripheral wall of the bottle mouth portion with the void part that communicates the inside and the outside of the bottle main body provided through the bottle mouth portion, and thus if a nebulizer adapter is attached to the bottle mouth portion of such a bottle to obtain a nebulizer configuration, the water droplets accumulated in the adapter without being induced to the outside can be returned to the bottle main body through the void part communicating the inside and the outside of the bottle main body. Furthermore, if a humidifier adapter is attached to the bottle mouth portion to obtain a humidifier configuration, the humidified gas discharged into the liquid stored in the bottle main body and guided on the water surface of the liquid is returned to the humidifier adapter through the void part, and supplied to the patient from the humidifier adapter.

In other words, in the nebulizer configuration, the nebulizer adapter and the bottle do not need to be connected with the drain tube as in the prior art, and the nebulizer can be effectively prevented from falling by hitting with the human hand, object, and the like. Since the drain tube does not need to be arranged in the nebulizer adapter, the handling of the task to screw-fit and connect the socket portion of the nebulizer adapter to the bottle mouth portion becomes extremely satisfactory, and the nebulizer adapter can be easily set to the bottle mouth portion since the task of connecting the drain tube is unnecessary. The port for connecting the drain tube to the bottle (in the humidifier configuration, the port for supplying the humidified gas humidified in the bottle to the outside) does not need to be separately formed, whereby the outer shape of the bottle can be simplified. As a result, the manufacturing of the bottle is facilitated and the bottle can be manufactured at low cost.

In such a bottle, the dip tube preferably includes a tube main body, and a fixing portion arranged at one end of the tube main body to be connected to the bottle mouth portion.

According to such a configuration, the dip tube and the bottle main body can be integrated with a very simple task of connecting the fixing portion to the bottle mouth portion.

The fixing portion preferably includes an annular body having a tube shape and arranged on the inner side of the bottle mouth portion, and a holding member which holds the tube main body on the inner side of the annular body, and the void part is preferably formed between an inner circumferential surface of the annular body and an outer circumferential surface of the tube main body. The annular body preferably includes a flange portion that fits into the upper end of the bottle mouth portion.

According to such a configuration, the upper end of the dip tube can be very easily arranged on the inner side of the peripheral wall of the bottle mouth portion with the void part that communicates the inside and the outside of the bottle main body arranged through the bottle mouth portion.

The outer circumferential surface at the lower end of the annular body is preferably arranged spaced apart from the inner peripheral surface of the bottle mouth portion.

According to such a configuration, when using the bottle as the nebulizer configuration, the water droplets returned from the nebulizer adapter to the bottle through the void part are flowed along the inner circumferential surface of the annular body and dropped toward the liquid in the bottle from the lower end of the annular body, so that the water droplets returned from the adapter can be prevented from attaching to the periphery of the inner peripheral surface of the bottle mouth portion. If the water droplets attach to the periphery of the inner peripheral surface of the bottle mouth portion, such droplets are less likely to drop (flow) downward and bacteria may increase. However, the breeding of bacteria can be effectively prevented at the periphery of the inner peripheral surface of the bottle mouth portion by adopting the configuration described above.

The holding member is a plate-like member or a rod-like member that extends along a vertical direction of the bottle mouth portion, and preferably connects the inner circumferential surface of the annular body and the outer circumferential surface of the tube main body.

According to such a configuration, the connection of the annular body and the tube main body can be made stronger without narrowing the flowing area of the void part (cross-sectional area at the horizontal cross-section of the void part) through which the humidified gas generated in the bottle flows or the water droplets flow. When using the bottle as the nebulizer configuration, the water droplets can be effectively guided to the tube main body so that the water droplets returned from the nebulizer adapter to the bottle through the void part flow along the outer surface of the tube main body. As a result, the water droplets returned to the bottle can be effectively prevented from accumulating at the periphery of the inner peripheral surface of the bottle mouth portion.

A diffuser portion is arranged at the other end of the tube main body, and is capable of discharging the gas supplied from one end of the tube main body into the liquid stored in the bottle main body as air bubbles.

According to such a configuration, the supplied gas can be efficiently humidified.

Effects of the Invention

According to the present invention, there is provided a bottle that can be used for the nebulizer or for the humidifier, and can return the water droplets accumulated in the nebulizer adapter without using the drain tube when used for the nebulizer, and a dip tube used in the bottle.

BRIEF DESCRIPTION OF THE DRAWINGS

FIG. 1 is a front view of a bottle according to one embodiment of the present invention.

FIG. 2 is a left side view of the bottle shown in FIG. 1.

FIG. 3 is a plan view of the bottle shown in FIG. 1.

FIG. 4 is a bottom view of the bottle shown in FIG. 1.

FIG. 5 is a cross-sectional view taken along line A-A of FIG. 3.

FIG. 6 is a cross-sectional view taken along line B-B of FIG. 3.

FIG. 7(*a*) is a schematic configuration perspective view of the dip tube shown in FIG. 5, FIG. 7(*b*) is a schematic configuration cross-sectional view of the dip tube, FIG. 7(*c*) is an enlarged plan view seen from the direction of an arrow C in FIG. 7(*b*), and FIG. 7(*d*) is a cross-sectional view taken along line D-D of FIG. 7(*c*).

FIG. 8(*a*) is an enlarged cross-sectional view of the main parts of a diffuser portion, and FIG. 8(*b*) is an enlarged front view of the main parts of the diffuser portion.

FIG. 9 is a cross-sectional view showing a state in which a humidifier adapter is connected to the bottle shown in FIG. 1.

FIG. 10 is a cross-sectional view showing a state in which a nebulizer adapter is connected to the bottle shown in FIG. 1.

FIG. 11 is a cross-sectional view showing a variant of the bottle shown in FIG. 1.

FIG. 12 is a schematic configuration diagram showing a prior art example.

FIG. 13(*a*) is a schematic configuration diagram of when the container shown in FIG. 12 is used as a container for the nebulizer, and FIG. 13(*b*) is a schematic configuration diagram of when the container shown in FIG. 12 is used as a container for the humidifier.

EMBODIMENTS OF THE INVENTION

Figure 1:
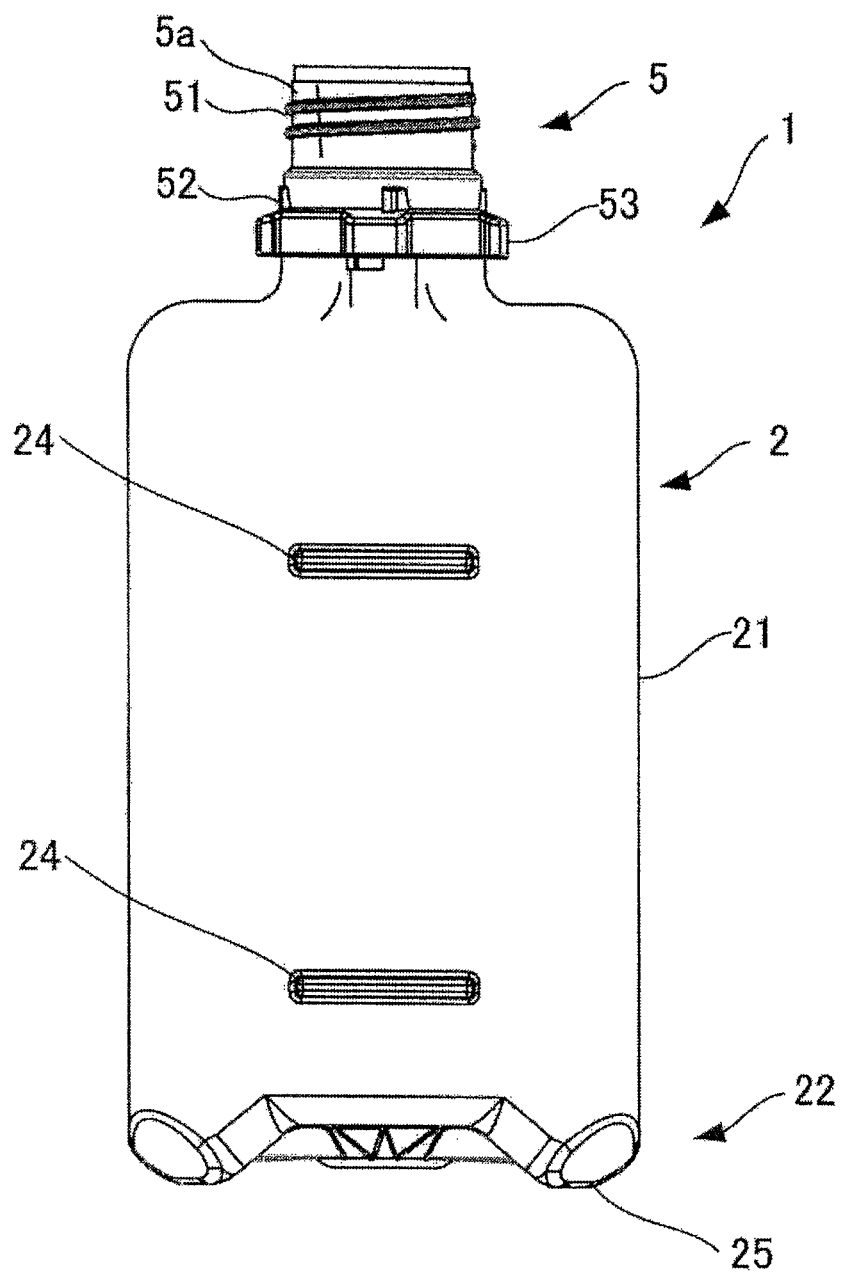
Figure 2:
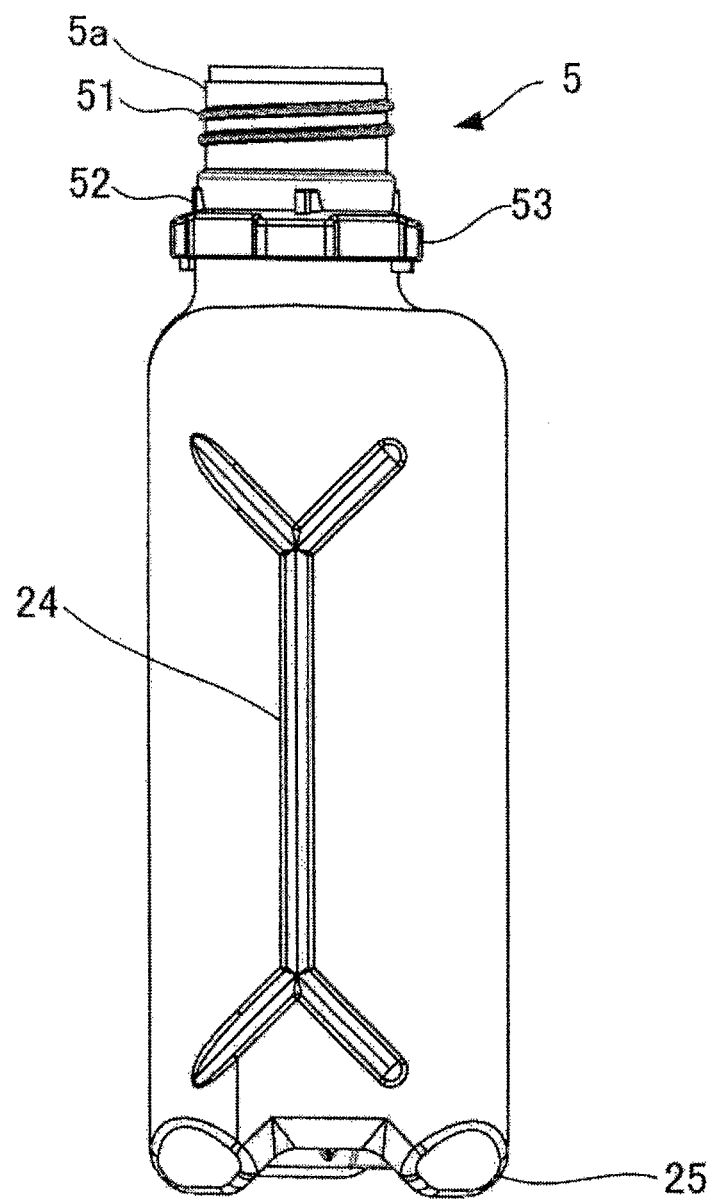
Figure 3:
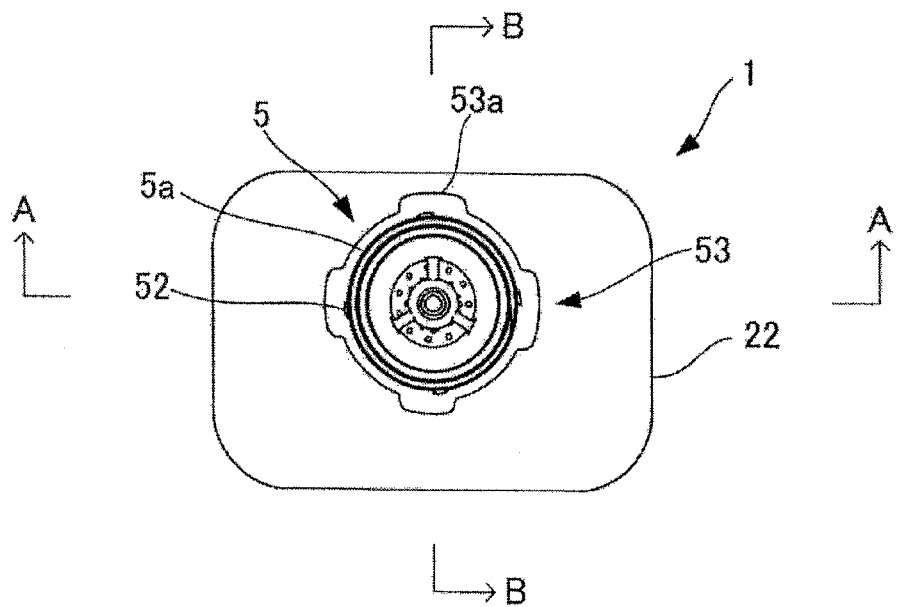
Figure 4:
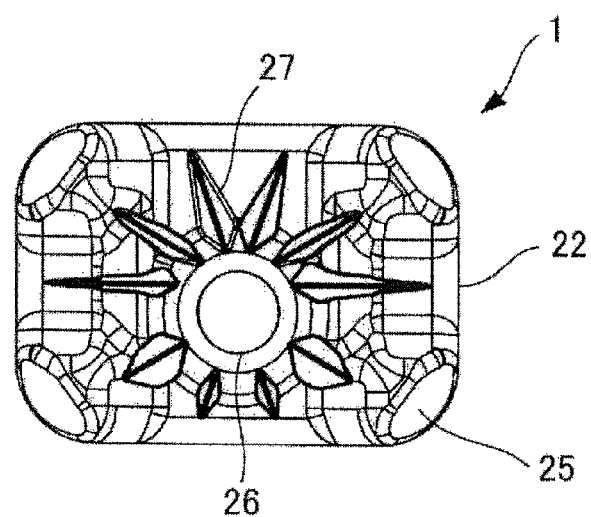
Figure 5:
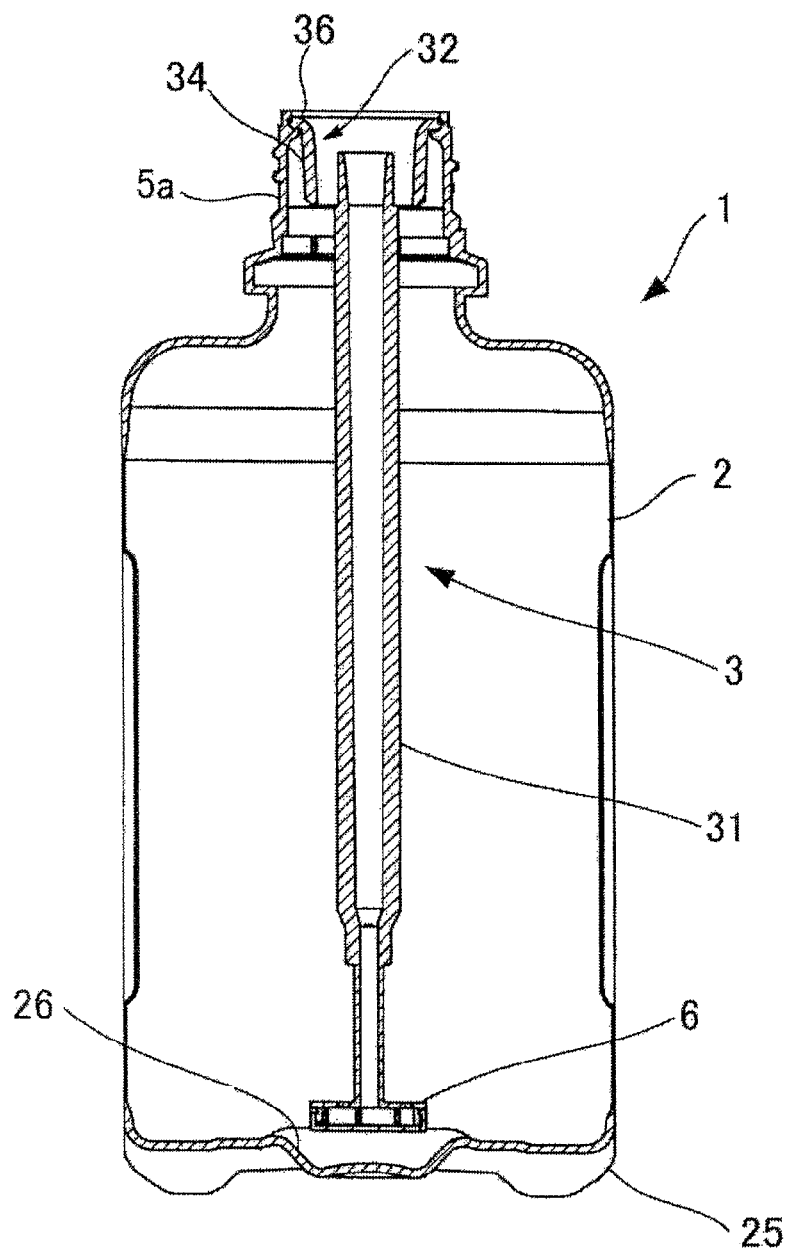
Figure 6:
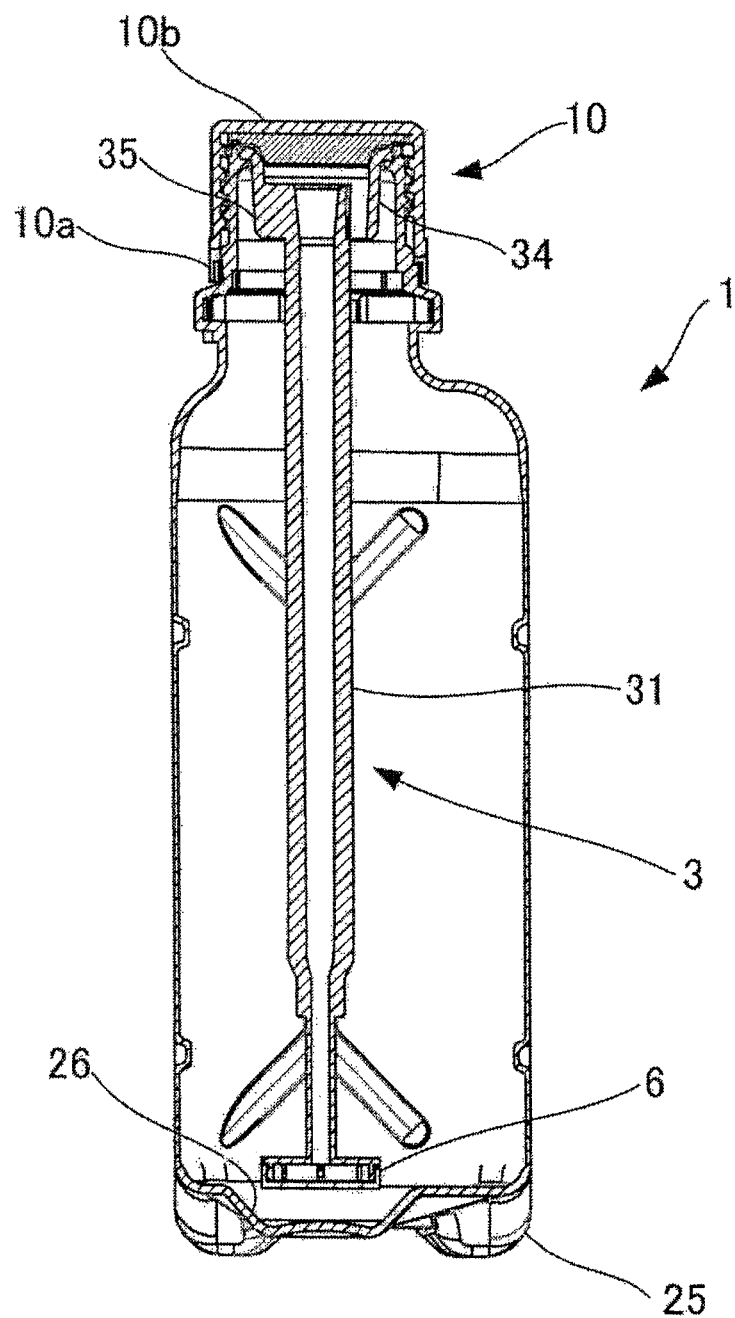

Hereinafter, a bottle according to an embodiment of the present invention will be described with reference to the accompanying drawings. FIG. 1 is a front view of a bottle according to one embodiment of the present invention, and FIG. 2 is a left side view thereof. FIG. 3 is a plan view of the bottle, and FIG. 4 is a bottom view thereof. FIG. 5 is a cross-sectional view taken along line A-A of FIG. 3, and FIG. 6 is a cross-sectional view taken along line B-B of FIG. 3.

A bottle 1 according to one embodiment of the present invention is, for example, a bottle to which a humidifying device adapter such a as a nebulizer adapter and a humidifier adapter for supplying humidified breathing gas is connected, and includes a bottle main body 2 and a dip tube 3, as shown in FIG. 1 to FIG. 6.

The bottle main body 2 includes a body portion 21 in which a horizontal cross-section is formed to a substantially rectangular shape, a bottom portion 22 that seals a lower end of the body portion 21, and a bottle mouth portion 5 arranged at an upper end of the body portion 21 by way of a shoulder portion. A volume reduction rib 24 configured by a single body of a linear recess or configured by combining a plurality of linear recesses is formed on each side surface of the body portion 21. The volume reduction rib 24 is a rib for folding the side surface of the body portion 21 when squashing the body portion 21. The front side and the back side of the body portion 21 are pushed to squash the bottle main body 2 to fold in a mountain folding manner along the volume reduction rib 24 formed at the side surfaces of the bottle main body 2, and then fold along the volume reduction rib 24 formed on the front side and the back side of the bottle 1 thus reducing the volume.

A leg portion 25 is arranged at the four corners of the bottom portion 22 of the bottle main body 2 to enhance the steadiness when the bottle 1 is placed. The leg portion 25 is formed to project outward from the bottom portion 22 toward the lower side in a vertical direction. A storing portion 26 having a circular shape in plan view, in which an interior bottom surface of the bottle main body 2 is depressed toward the lower side in the vertical direction, is formed at a central region of the bottom portion 22 of the bottle main body 2. The storing portion 26 is formed such that a center in plan view overlaps an axis center of the bottle mouth portion 5. A pressure withstanding rib 27 is formed at a periphery of the storing portion 26 to surround the storing portion 26. The pressure withstanding rib 27 is formed to project outward from the bottom portion 22 of the bottle main body 2 toward the lower side in the vertical direction. The pressure withstanding rib 27 is arranged to prevent deformation such as expansion of the bottom portion 22 of the bottle 1 from pressure inside the bottle 1 when the interior of the bottle 1 is filled with content liquid and inactive gas such as nitrogen and the bottle 1 is closed.

The bottle mouth portion 5 includes a screw part 51 that is arranged at an upper part of the bottle main body 2 and that enables a lid 10 (see FIG. 6) having a screw structure to be attached thereto. The screw part 51 is formed on an outer peripheral surface of a peripheral wall 5a of the bottle mouth portion 5. Since a separation type lid 10 (virgin cap), which is opened by ripping the lower end, is attached, the peripheral wall 5a on the lower side of the screw part 51 is formed to a thick structure, and a projection 52 serving as a stopper is arranged in plurals on an outer peripheral part of the thick structure. In other words, when the separation type lid is turned to open, a ring part 10a at the lower part gets caught at the projection thus remaining on the outer periphery of the thick structure, and only a lid main body 10b at the upper part is separated. According to such a configuration, the bottle 1 according to the present embodiment is a structure that can be sealed, and in which sterilization processing can be performed.

The bottle mouth portion 5 includes an engagement part 53 on a lower side of the thick structure formed with the projection 52 serving as the stopper. The engagement part 53 is configured as a collection of a plurality of projecting bodies 53a projecting outward in a horizontal direction from the peripheral wall 5a of the bottle mouth portion 5. A socket portion in the humidifying device adapter such as the nebulizer adapter and the humidifier adapter is fitted to the engagement part.

Various materials can be used for a material forming the bottle main body 2, but olefin polymer, for example, is used herein. The representative olefin polymer is polyethylene and polypropylene polymer. Examples of the polyethylene include high density polyethylene (HDPE), low density polyethylene (LDPE), and a blend (HDPE/LDPE) of the same. Examples of the polypropylene polymer include polypropylene, a random (or block) copolymer of polypropylene and other □-olefin such as ethylene, syndiotactic polypropylene, and the blend of the same.

The dip tube 3 is a tubular body that is dipped in the liquid stored in the bottle main body 2, and includes a tube main body 31, a fixing portion 32, and a diffuser portion 6, as shown in FIG. 1 to FIG. 6, and FIG. 7. FIG. 7($a$) is a perspective view of a schematic configuration of the dip tube 3, and FIG. 7($b$) is a cross-sectional view of a schematic configuration of the dip tube. FIG. 7($c$) is an enlarged plan view seen from the direction of an arrow C in FIG. 7($b$), and FIG. 7($d$) is a cross-sectional view taken along line D-D of FIG. 7($c$).

The tube main body 31 is configured by a linear pipe, where the fixing portion 32 is connected to one end (upper end), and the diffuser portion 6 is connected to the other end (lower end). The tube main body 31 is configured such that a diameter reduces to ensure space for forming a first through-hole 66 in the vicinity of the other end. The length of the tube main body 31 is set such that the other end becomes proximate to the bottom portion 22 of the bottle main body 2 when the one end is arranged on the inner side of the bottle mouth portion 5 (in the region surrounded by the peripheral wall 5a).

The fixing portion 32 is a member for installing the dip tube 3 in the bottle 1, and includes an annular body 34 having a tubular shape and arranged on the inner side of the bottle mouth portion 5, and a holding member 35 for holding and fixing the tube main body 31 on the inner side of the annular body 34. The annular body 34 is arranged at a position where its axis center substantially overlaps the axis center of the bottle mouth portion 5. A flange portion 36 is arranged at an upper end of the annular body 34, and the dip tube 3 can be installed in the bottle main body 2 by fitting the flange portion 36 to the upper end of the bottle mouth portion 5. To form a space between the outer circumferential surface of the annular body 34 and the inner peripheral surface of the bottle mouth portion 5 (inner peripheral surface of the peripheral wall 5a), the annular body 34 is arranged on the inner side of the bottle mouth portion 5 so that the outer circumferential surface of the annular body 34 and the inner peripheral surface of the bottle mouth portion 5 are spaced apart from each other.

The holding member 35 is a plate member that extends along the vertical direction of the bottle mouth portion 5, and connects and fixes the inner circumferential surface of the annular body 34 and the outer circumferential surface of the tube main body 31. In the present embodiment, the tube main body 31 and the annular body 34 are coupled by three holding members 35 arranged with a predetermined interval along the circumferential direction of the inner circumferential surface of the annular body 34 (or outer circumferential surface of the tube main body 31). According to such a configuration, a void part 37 for communicating the inside and outside of the bottle main body 2 (void part 37 for communicating the ends of the annular body 34) is formed between the holding members 35 arranged between the inner circumferential surface of the annular body 34 and the outer circumferential surface of the tube main body 31. In the present embodiment, the tube main body 31 and the annular body 34 are coupled by three holding members 35, but the number of holding members 35 is not particularly limited, and for example, the tube main body 31 and the annular body 34 may be coupled with one or two holding members 35, or with four or more holding members 35.

Figure 8A:
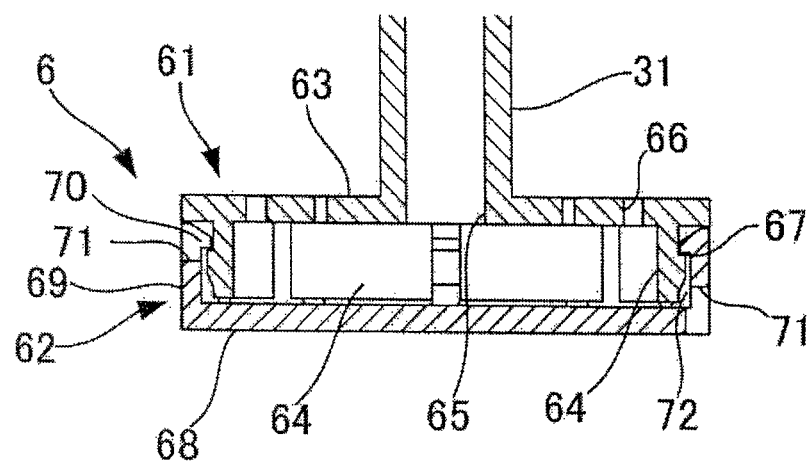
Figure 8B:
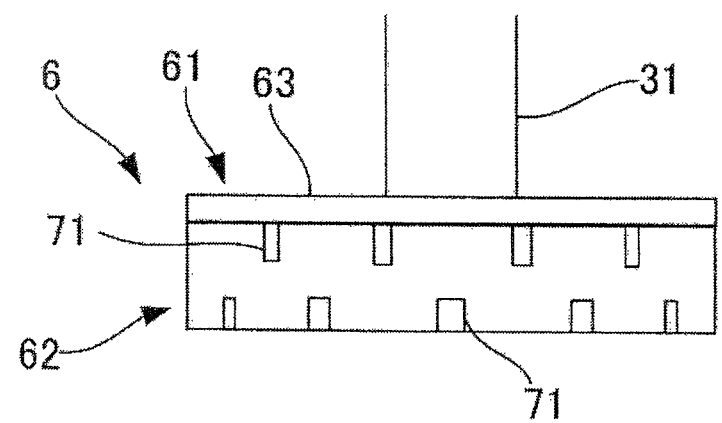

The diffuser portion 6 is a member having a function of discharging gas supplied through the inside of the tube main body 31 into the liquid stored in the bottle main body 2 as air bubbles, or on the other hand, a function of guiding the liquid stored in the bottle main body 2 into the tube main body 31, and is connected to the other end of the tube main body 31. The diffuser portion 6 is arranged immediately above the storing portion 26 formed at the bottom portion 22 of the bottle main body 2 in a state that the dip tube 3 is installed in the bottle main body 2, as shown in FIG. 5 and FIG. 6. The diffuser portion 6 may be configured integrally with the tube main body 31 or may be configured to be detachably attached to the tube main body 31. As shown in the enlarged cross-sectional view of the main parts of FIG. 8, the diffuser portion 6 includes an upper housing 61 and a lower housing 62. FIG. 8(a) is an enlarged cross-sectional view of the main parts of the diffuser portion 6, and FIG. 8(b) is an enlarged front view of the main parts of the diffuser portion 6.

The upper housing 61 includes a plate body 63 having a circular shape in plan view in which one surface side connects to a lower end of the tube main body 31, and a plurality of side wall portions 64 arranged in an upright manner on the other surface of the plate body 63. A slit is formed between the side wall portions 64. An opening 65 that passes through the plate body 63 is formed at a central part of the plate body 63, and the tube main body 31 and the plate body 63 are connected such that the center of the opening 65 and the axis center of the tube main body 31 coincide. An opening diameter of the opening 65 and the inner diameter of the tube main body 31 are formed to have substantially the same dimension. A plurality of tiny first through-holes 66 that passes through the plate body 63 is formed at a periphery of the opening 65 formed at the central part of the plate body 63. The plurality of first through-holes 66 are arranged on a circumference having the axis center of the tube main body 31 as a center. The hole diameter of the first through-hole 66 is formed to become larger as the formed position of the first through-hole 66 becomes distant from the opening 65 to allow the air bubbles to easily flow out. The side wall portions 64 are arranged with a predetermined interval in the vicinity of the peripheral edge of the plate body 63 along the circumferential direction of the plate body 63. A fit-in recess 67 that engages a fit-in projection 70 of the lower housing 62 is formed at the outer peripheral part of the side wall portion 64.

The lower housing 62 includes a plate-like lid portion 68 having a circular shape in plan view that covers a region surrounded by the side wall portions 64 of the upper housing 61, and a tubular peripheral wall portion 69 arranged in an upright manner from the peripheral edge of the lid portion 68. The fit-in projection 70 that engages the fit-in recess 67 formed on the outer peripheral surface of the side wall portion 64 of the upper housing 61 is formed on the inner surface of the peripheral wall portion 69. The peripheral wall portion 69 is formed with a plurality of second through-holes 71 that passes through the peripheral wall portion 69. The second through-holes 71 are formed with a predetermined interval along the circumferential direction of the peripheral wall portion 69. The second through-holes 71 are respectively formed at the upper end and the lower end of the peripheral wall portion 69.

When the lower housing 62 is installed on the upper housing 61, the peripheral wall portion 69 of the lower housing 62 is arranged on the outer side of the side wall portion 64 of the upper housing 61, and the peripheral wall portion 69 and the side wall portion 64 are formed between the inner peripheral surface of the peripheral wall portion 69 of the lower housing 62 and the outer peripheral surface of the side wall portion 64 of the upper housing 61 so as to form a gap 72. The gas such as oxygen supplied through the inside of the tube main body 31 is discharged into the liquid stored in the bottle main body 2 from the plurality of first through-holes 66 and the second through-holes 71. The gas discharged from the second through-hole 71 is passed through the slit formed between the side wall portions 64 and the gap 72, and discharged from the through-hole 71. The gas can be evenly flowed out from each of the second through-holes 71 to the outside without bias by guiding the gas to the second through-hole 71 through the gap 72. The lower housing 62 may be installed on the upper housing 61 so that the slit formed between the side wall portions 64 in the upper housing 61 and the second through-hole 71 formed in the lower housing 62 do not overlap each other, or the lower housing 62 may be installed on the upper housing 61 so that a part of the slit and a part of the second through-hole 71 overlap each other. If the lower housing 62 is installed on the upper housing 61 so that a part of the slit and a part of the second through-hole 71 overlap each other, some of the gas such as oxygen supplied through the inside of the tube main body 31 is directly guided to the second through-hole 71 through the slit and discharged into the liquid stored in the bottle main body 2.

In the present embodiment, the peripheral wall portion 69 of the lower housing 62 is configured to be arranged on the outer side of the side wall portion 64 of the upper housing 61, but is not particularly limited to such a configuration, and the peripheral wall portion 69 of the lower housing 62 may be configured to be arranged on the inner side of the side wall portion 64 of the upper housing 61. When adopting such a configuration, a plural of slits, each extending in a direction along the axis center of the tube main body 31, is preferably formed in the peripheral wall portion 69 of the lower housing 62, and the side wall portion 64 of the upper housing 61 is preferably formed to a tubular shape.

Figure 9:
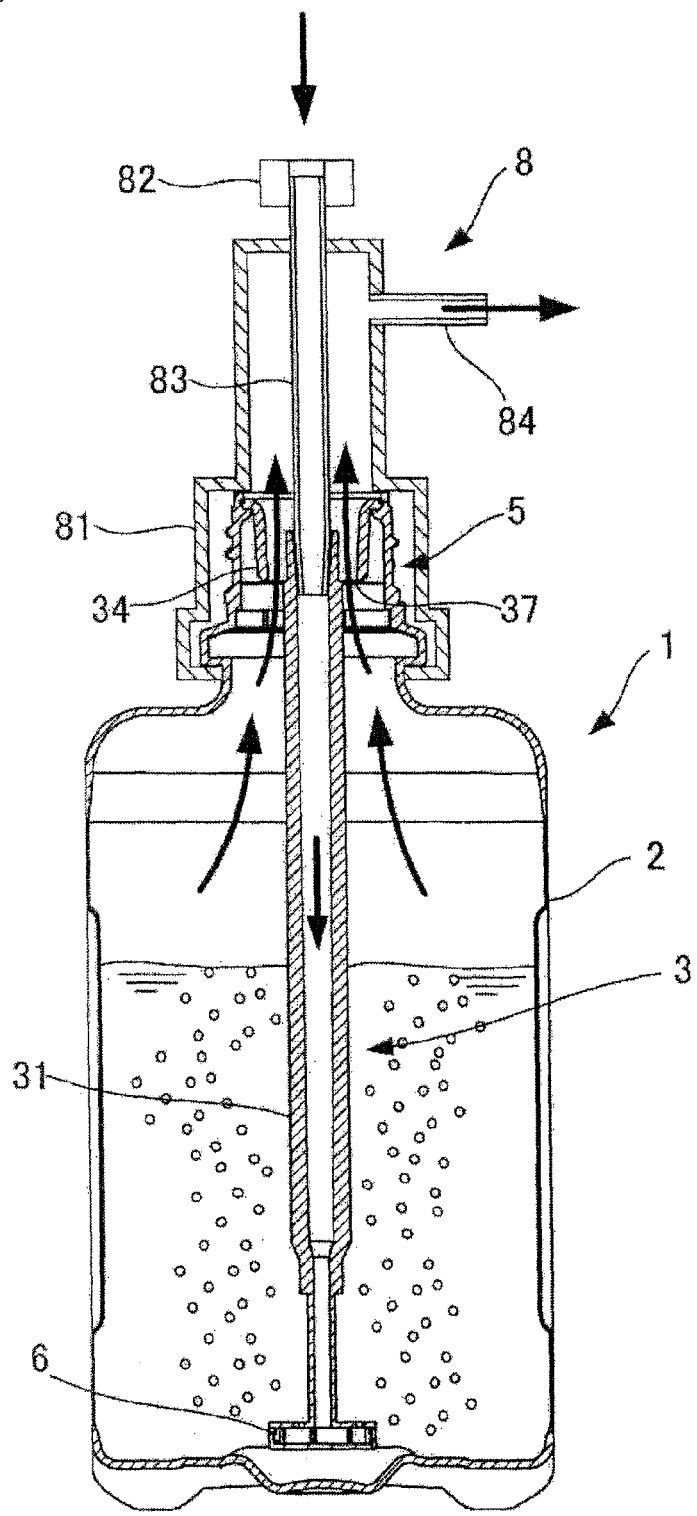

The operation of the bottle 1 according to the present embodiment of when attaching the humidifier adapter, which is the humidifying device adapter, to the bottle 1 for use as a humidifier will be hereinafter described. FIG. 9 is a schematic configuration cross-sectional view showing a state in which a humidifier adapter 8 is connected to the bottle 1. A solution dissolved with medicinal agent, and liquid such as sterilized water, purified water, distilled water, normal saline solution is stored in the bottle 1.

The humidifier adapter 8 is a device for communicating a gas supply source (not shown) of air, oxygen, and like to the bottle 1, and includes a tubular socket portion 81 installed to cover the bottle mouth portion 5 of the bottle 1, a gas piping attachment portion 82, to which the piping connected to the gas supply source is attached, a tubular flow path tube 83 arranged in the socket portion 81, and a gas flow-out port 84, to which a tube (not shown) for guiding the gas added with moisture to the supplying destination. When the humidifier adapter 8 is connected to the bottle mouth portion 5, the flow path tube 83 is communicated and connected to the tube main body 31 of the dip tube 3.

First, gas is supplied from the gas supply source (e.g., oxygen tank) (not shown). The supplied gas is guided to the flow path tube 83 through the gas piping attachment portion 82, and supplied into the tube main body 31 of the dip tube 3. The gas supplied into the tube main body 31 is discharged into the water inside the bottle main body 2 from the first through-hole 66 and the second through-hole 71 formed in the diffuser portion 6. The discharged gas becomes microscopic air bubbles when passing through the first through-holes 66 and the second through-holes 71, and rises in the water. In the course of rising in the water, the air bubbles are sufficiently and efficiently added with moisture (water vapor and mist water), and guided to a space on the water surface of the water stored inside the bottle main body 2 as humidified gas. Thereafter, the gas is passed through the void part 37 formed between the annular body 34 in the fixing portion 32 and the tube main body 31 of the dip tube 3 arranged at the bottle mouth portion 5, and guided to the socket portion 81. The humidified gas guided to the socket portion 81 is fed to the patient through the gas flow-out port 84 and the tube (not shown).

Figure 10:
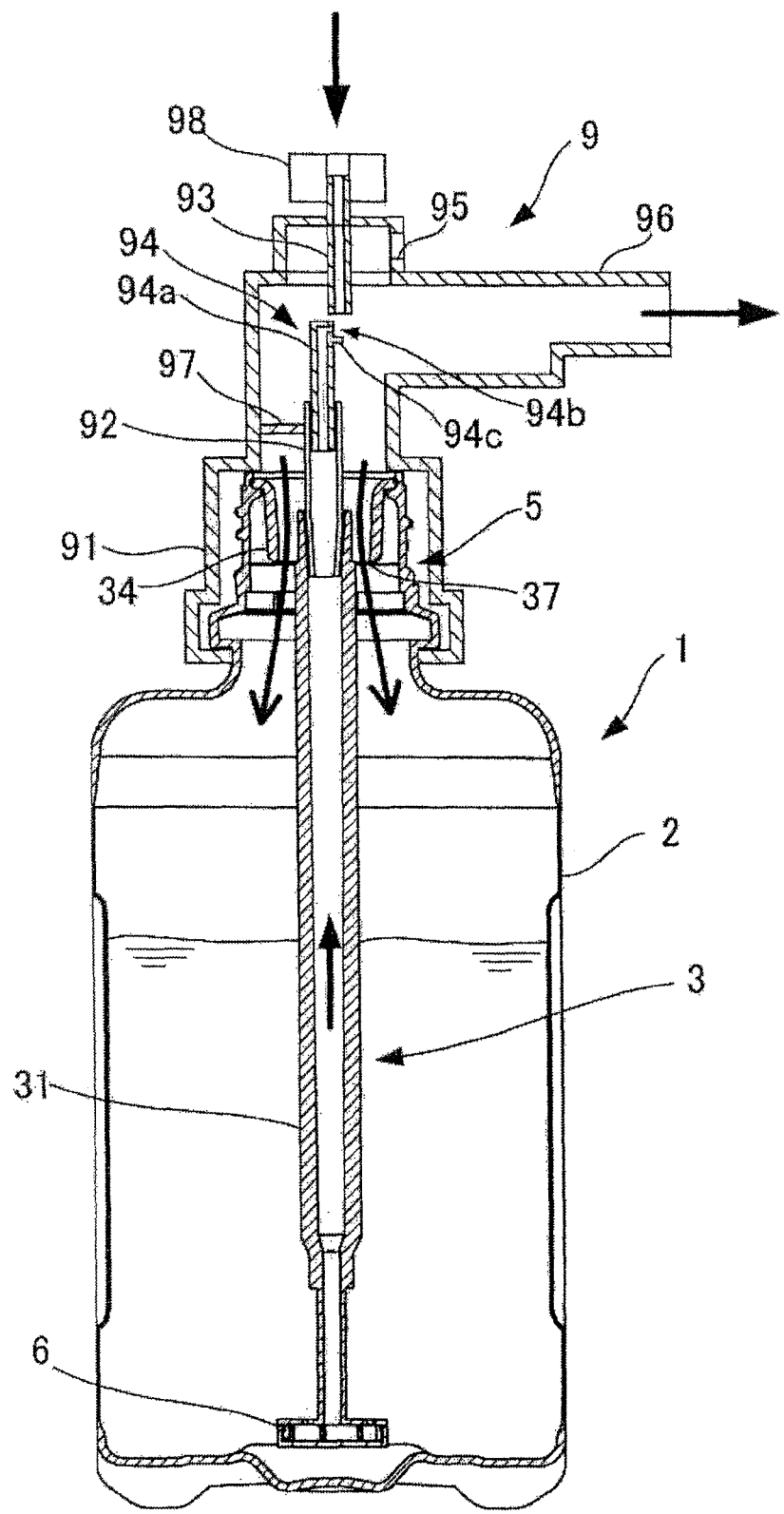

The operation of the bottle 1 when the nebulizer adapter 9, which is the humidifying device adapter, is attached to the bottle 1 and used as the nebulizer will now be described below. FIG. 10 is a schematic configuration cross-sectional view showing a state in which the nebulizer adapter 9 is connected to the bottle 1. A solution dissolved with medicinal agent, and liquid such as sterilized water, purified water, distilled water, normal saline solution, and the like is stored in the bottle 1.

The nebulizer adapter 9 includes a socket portion 91, a flow path tube 92, a nozzle portion 93, an aerosol forming member 94, an air suction hole 95, and an inducing portion 96. The socket portion 91 is a tubular member that connects to the bottle mouth portion 5 of the bottle 1 so as to cover the same. The flow-path tube 92 is a tubular body to be communicated and connected to the dip tube 3 of the bottle 1 with the socket portion 91 connected to the bottle mouth portion 5, and is fixed inside the socket portion 91 by a rod-shaped fixing member 97 for connecting the outer peripheral surface of the flow-path tube 92 and the inner peripheral surface of the tubular socket portion 91. The nozzle portion 93 is a tubular body that injects oxygen gas from the lower end, and includes a connecting portion 98 to connect to the gas supply source (not shown) at the upper end. The aerosol forming member 94 is a member that is arranged in the gas injecting direction of the nozzle portion 93, and that aspirates the sterilized water through the dip tube 3 and the flow-path tube 92 by the airflow of the injected gas and generates microscopic aerosol from the aspirated sterilized water. Specifically, the aerosol forming member 9 includes a pipe body 94a in which the upper end is closed, a through-hole 94b formed near the upper end of the pipe body 94a and communicated to the interior tube path, and a projecting member 94c arranged on the surface of the pipe body 94a on the lower side of the through-hole 94b and projected outward. The pipe body 94a is communicated and connected with the flow-path tube 92 at the lower end. The air suction hole 95 is a hole that suctions the air with the injection of gas by the nozzle portion 93. The inducing portion 96 is a tubular member that is arranged on the side surface of the socket portion 91, and that again induces the mixed gas of oxygen containing aerosol and air to the outside.

When the oxygen gas supplied from the gas supply source (not shown) is injected from the nozzle portion 93 toward the projecting member 94c, the interior of the socket portion 91 becomes a negative pressure state by the airflow of the injected gas, so that the sterilized water (liquid) contained in the bottle 1 is aspirated and flowed out from the through-hole 94b through the diffuser portion 6, the dip tube 3, the flow-path tube 92, and the aerosol forming member 94. The sterilized water (liquid) that flowed out becomes microscopic aerosol due to the action of the oxygen gas striking the projecting member 94c. The aerosol is mixed with oxygen gas, and further mixed with the air suctioned from the air suction hole 95 and induced to the outside through the inducing portion 96 to be supplied to the patient.

Among the sterilized water (liquid) that flowed out from the through-hole 94b through the diffuser portion 6, the dip tube 3, the flow-path tube 92, and the aerosol forming member 94, the water droplets that did not become the aerosol drop inside the socket portion 91 and return to the bottle main body 2 through the void part 37 formed in the bottle mouth portion 5. The water droplets accumulated at the bottom of the inducing portion 96 also drop inside the socket portion 91 and return to the bottle main body 2 through the void part 37 formed in the bottle mouth portion 5.

The bottle 1 according to the present embodiment has a structure in which the upper end of the dip tube 3, arranged inside the bottle main body 2, is arranged on the inner side of the peripheral wall 5a of the bottle mouth portion 5 with the void part 37 that communicates the inside and the outside of the bottle main body 2 provided through the bottle mouth portion 5, so that if the nebulizer adapter is attached to the bottle mouth portion 5 of the bottle 1 to obtain the nebulizer configuration, the water droplets accumulated in the adapter can be returned to the inside of the bottle main body 2 through the void part 37 communicating the inside and the outside of the bottle main body 2 without being induced to the outside. If the humidifier adapter is attached to the bottle mouth portion 5 to obtain the humidifier configuration, the humidified gas discharged into the liquid stored in the bottle main body 2 and guided on the water surface of the liquid is returned to the humidifier adapter through the void part 37, and supplied to the patient from the humidifier adapter.

In other words, in the nebulizer configuration, the nebulizer adapter and the bottle 1 do not need to be connected with the drain tube, whereby an event in which the human hand, object, and the like get caught at the drain tube, which can prevent the nebulizer form falling effectively. Furthermore, since the nebulizer adapter does not need to include the drain tube, the handling of the task to screw-fit and connect the socket portion 91 of the nebulizer adapter to the bottle mouth portion 5 becomes extremely satisfactory, and moreover, the nebulizer adapter can be easily set to the bottle mouth portion 5 since the connecting task of the drain tube is unnecessary. The port for connecting the drain tube to the bottle 1 (in the humidifier configuration, the port for supplying the humidified gas humidified in the bottle 1 to the outside) does not need to be separately formed, and hence the outer shape of the bottle 1 can be simplified. As a result, the manufacturing of the bottle 1 is facilitated and the bottle 1 can be manufactured at low cost.

The dip tube 3 includes the tube main body 31, and the fixing portion 32 arranged at one end of the tube main body 31 to be connected to the bottle mouth portion 5, so that the dip tube 3 and the bottle main body 2 can be integrated through an extremely simple task of connecting the fixing portion 32 to the bottle mouth portion 5.

The fixing portion 32 includes the annular body 34 having a tubular shape and arranged on the inner side of the bottle mouth portion 5 and the holding member 35 for holding the tube main body 31 on the inner side of the annular body 34, where the void part 37 is formed between the inner circumferential surface of the annular body 34 and the outer circumferential surface of the tube main body 31. According to such a configuration, the upper end of the dip tube 3 can be easily arranged on the inner side of the peripheral wall 5a of the bottle mouth portion 5 with the void part 37 that communicates the inside and the outside of the bottle main body 2 arranged through the bottle mouth portion 5.

The annular body 34 includes the flange portion 36 that fits to the upper end of the bottle mouth portion 5, and thus the installation task of the dip tube 3 to the bottle main body 2 can be very easily carried out.

The outer circumferential surface at the lower end of the annular body 34 is arranged spaced apart from the inner peripheral surface of the bottle mouth portion 5 so that when using the bottle 1 as the nebulizer configuration, the water droplets returned from the inside of the nebulizer adapter to the bottle 1 through the void part 37 flow down along the inner circumferential surface of the annular body 34 and drop toward the liquid in the bottle 1 from the lower end of the annular body 34. The water droplets returned from the adapter can be effectively prevented from attaching to the periphery of the inner peripheral surface of the bottle mouth portion 5. If the water droplets attach to the periphery of the inner peripheral surface of the bottle mouth portion 5, such water droplets are less likely to drop (flow) downward and bacteria may increase. However, the breeding of bacteria can be effectively prevented at the periphery of the inner peripheral surface of the bottle mouth portion 5 by adopting the configuration described above.

The holding member 35 is a plate-like member that extends along the vertical direction of the bottle mouth portion 5, and is configured to connect the inner circumferential surface of the annular body 34 and the outer circumferential surface of the tube main body 31. According to such a configuration, the connection of the annular body 34 and the tube main body 31 becomes stronger without narrowing the flowing area of the void part 37 (cross-sectional area at the horizontal cross-section of the void part 37) through which the humidified gas generated in the bottle 1 flows or the water droplets flow.

Figure 11:
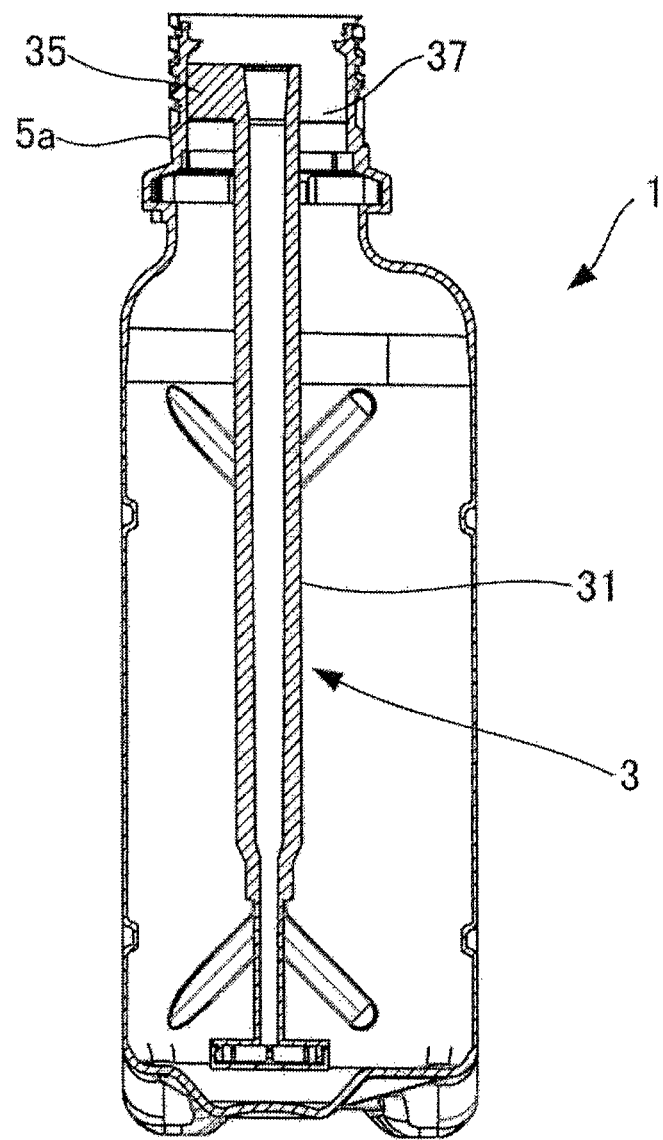

The embodiment of the bottle 1 according to the present invention has been described above, but the specific configuration is not limited to such an embodiment. For example, the upper end of the dip tube 3 arranged inside the bottle 1 may be arranged on the inner side of the peripheral wall 5a of the bottle mouth portion 5 with the void part 37 that communicates the inside and the outside of the bottle main body 2 arranged through the bottle mouth portion 5, and for example, the dip tube 3 can be configured as a structure shown in FIG. 11. The dip tube 3 shown in FIG. 11 is configured by the tube main body 31 and the holding member 35. The holding member 35 shown in FIG. 11 has a function serving as the fixing portion 32, and is formed to connect the inner peripheral surface of the peripheral wall 5a at the bottle mouth portion 5 and the outer circumferential surface of the tube main body 31. When such a configuration is adopted, the holding member 35 is preferably configured by the plate-like member extending along the vertical direction of the bottle mouth portion 5. According to such a configuration, when using the bottle 1 as the nebulizer configuration, the water droplets can be effectively guided to the tube main body 31 so that the water droplets returned from the inside of the nebulizer adapter to the bottle 1 through the void part 37 flow down along the outer surface of the tube main body 31. As a result, the water droplets returned to the bottle 1 can be effectively prevented from accumulating at the periphery of the inner peripheral surface of the bottle mouth portion 5.

The bottle 1 in the embodiment described above has a configuration in which the annular body 34 including the fixing portion 32 includes the flange portion 36 that fits to the upper end of the bottle mouth portion 5, but for example, a configuration in which the flange portion 36 is omitted, the annular body 34 is pushed into the inner side of the bottle mouth portion 5, and the outer circumferential surface of the annular body 34 is fitted to the inner peripheral surface of the bottle mouth portion 5 may be adopted. If such a configuration is adopted, the lower end of the annular body 34 is preferably configured to reduce the diameter such as by arranging a tapered portion, for example, so that the outer circumferential surface at the lower end of the annular body 34 is spaced apart from the inner peripheral surface of the bottle mouth portion 5. With the configuration of reducing the diameter of the lower end of the annular body 34, the water droplets returned from the nebulizer adapter can be prevented from attaching to the periphery of the inner peripheral surface of the bottle mouth portion 5 when using the bottle 1 for the nebulizer configuration.

In the embodiment described above, the holding member 35 for connecting and fixing the inner circumferential surface of the annular body 34 and the outer circumferential surface of the tube main body 31 is configured by a plate-like member extending along the vertical direction of the bottle mouth portion 5, but is not particularly limited to such a configuration, and the holding member 35 may be configured by a rod-shaped member to connect the annular body 34 and the tube main body 31.

DESCRIPTION OF REFERENCE SIGNS 1 bottle
2 bottle main body
5 bottle mouth portion
3 dip tube
31 tube main body
32 fixing portion
34 annular body
35 holding member
36 flange portion
37 void part

The invention claimed is:
1. A bottle comprising,
a bottle main body having a bottle mouth portion at an upper part, and
a dip tube dipped into a liquid stored in the bottle main body, wherein
an upper end of the dip tube is arranged on an inner side of a peripheral wall of the bottle mouth portion with a void part that communicates inside and outside of the bottle main body provided through the bottle mouth portion,
the dip tube includes a tube main body, and a fixing portion arranged at one end of the tube main body to be connected to the bottle mouth portion,
the fixing portion includes an annular body having a tubular shape and arranged on the inner side of the bottle mouth portion, and a holding member which holds the tube main body on an inner side of the annular body, and the void part is formed between an inner circumferential surface of the annular body and an outer circumferential surface of the tube main body, and the holding member is a plate-like member or a rod-like member that extends along a vertical direction of the bottle mouth portion, and connects the inner circumferential surface of the annular body and the outer circumferential surface of the tube main body.

2. The bottle according to claim 1, wherein the annular body includes a flange portion that fits into an upper end of the bottle mouth portion.

3. The bottle according to claim 2, wherein an outer circumferential surface at a lower end of the annular body is arranged spaced apart from an inner peripheral surface of the bottle mouth portion.

4. The bottle according to claim 1, wherein a diffuser portion is arranged at the other end of the tube main body, and is adapted to discharge gas supplied from one end of the tube main body into the liquid stored in the bottle main body as air bubbles.

5. The bottle according to claim 2, wherein a diffuser portion is arranged at the other end of the tube main body, and is adapted to discharge gas supplied from one end of the tube main body into the liquid stored in the bottle main body as air bubbles.

6. The bottle according to claim 3, wherein a diffuser portion is arranged at the other end of the tube main body, and is adapted to discharge gas supplied from one end of the tube main body into the liquid stored in the bottle main body as air bubbles.

7. A dip tube comprising a tube main body and a fixing portion arranged at one end of the tube main body, wherein the fixing portion includes an annular body having a tubular shape and a holding member that holds the tube main body on an inner side of the annular body, a void part that communicates the ends of the annular body is formed between an inner circumferential surface of the annular body and an outer circumferential surface of the tube main body, and the holding member is a plate-like member or a rod-like member, and connects the inner circumferential surface of the annular body and the outer circumferential surface of the tube main body.

8. The dip tube according to claim 7, further comprising a diffuser portion for discharging gas supplied from one end of the dip tube, wherein the diffuser portion includes an upper housing connected to the other end of the tube main body and a lower housing attached to the upper housing, the upper housing includes a plate body in which one surface side connects to the tube main body, and a side wall portion arranged in an upright manner on the other surface of the plate body, the lower housing includes a lid that covers a region surrounded by the side wall portions of the upper housing, and a peripheral wall portion arranged in an upright manner from a peripheral edge of the lid and formed with a through-hole, and the lower housing is attached to the upper housing with the peripheral wall portion arranged on an outer side of the side wall portion and a gap formed between the side wall portion and the peripheral wall portion.

\* \* \* \* \*